United States Patent
Hussey (10) Patent No.: US 7,137,153 B2
(45) Date of Patent: *Nov. 21, 2006

(54) SPORT GOGGLE WITH IMPROVED VENTILATION

(75) Inventor: Patrick P. Hussey, Carlsbad, CA (US)

(73) Assignee: K-2 Corporation, Seattle, WA (US)

( * ) Notice: Subject to any disclaimer, the term of this patent is extended or adjusted under 35 U.S.C. 154(b) by 258 days.

This patent is subject to a terminal disclaimer.

(21) Appl. No.: 10/695,055

(22) Filed: Oct. 27, 2003

(65) Prior Publication Data

US 2004/0103469 A1    Jun. 3, 2004

Related U.S. Application Data

(63) Continuation-in-part of application No. 10/098,980, filed on Mar. 15, 2002, now Pat. No. 6,637,038.

(51) Int. Cl.
   *A61F 9/02*    (2006.01)
(52) U.S. Cl. .......................................... 2/437
(58) Field of Classification Search ................... 2/431, 2/440–446, 436, 437
   See application file for complete search history.

(56) References Cited

U.S. PATENT DOCUMENTS

| | | | |
|---|---|---|---|
| 1,947,137 A | 2/1934 | Fraser | |
| 2,409,286 A | 10/1946 | Joyce | |
| 3,141,172 A | 7/1964 | Hirschmann | |
| 3,418,658 A | 12/1968 | Danico | |
| 3,517,393 A | 6/1970 | Beauchef | |
| 4,141,085 A | 2/1979 | Adams, Sr. | |
| 4,172,455 A | 10/1979 | Beaussant | |
| 4,290,673 A | 9/1981 | Yamamoto | |
| 4,649,577 A | 3/1987 | Wiedner | |
| 4,653,124 A | 3/1987 | McNeal et al. | |
| 4,670,914 A | 6/1987 | Harris | |
| 4,706,746 A | 11/1987 | White et al. | |
| 4,877,320 A | 10/1989 | Holden | |
| 4,977,626 A | 12/1990 | Smith | |
| 5,363,512 A | 11/1994 | Grabos, Jr. et al. | |
| 5,452,480 A | 9/1995 | Ryden | |
| 5,519,896 A | 5/1996 | Ford | |
| 5,542,130 A | 8/1996 | Grabos, Jr. et al. | |
| 5,610,668 A | 3/1997 | Mage | |

(Continued)

*Primary Examiner*—Katherine M. Moran
(74) *Attorney, Agent, or Firm*—Christensen O'Connor Johnson Kindness PLLC (57) ABSTRACT

An improved sport goggle for skiing, motorcycling, paintball, racing, and other sports featuring apertures communicating with a pressurized air flow provided by focusing channels in a ledge projecting from the goggle body thereby increasing air flow into the eye cavity of the goggle through the apertures. Venting of the eye cavity of the sport goggle is aided by forming of the goggle body shape to create low pressure zones adjacent to side and top venting apertures that communicate with the eye cavity. During use by a user, wind and forward motion creates air flow onto the focusing channel which focuses the divergent entering air upon a point adjacent to lower intake apertures thereby increasing the air pressure entering the goggle. Air circulation through the eye cavity is additionally aided by the curved shape of the goggle body creating low pressure zones adjacent to venting apertures to pull air from the eye cavity thereby increasing air flow and eliminating fogging. Additional utility is provided by aperture gates which are cooperatively engageable with the venting apertures to regulate air flow and/or absorb moisture.

34 Claims, 3 Drawing Sheets

U.S. PATENT DOCUMENTS

| | | |
|---|---|---|
| 5,652,956 A | 8/1997 | Hoshizaki et al. |
| 5,657,106 A | 8/1997 | Herald, Jr. et al. |
| 5,771,499 A | 6/1998 | Monaco et al. |
| 5,898,468 A | 4/1999 | Mage |
| 5,966,746 A | 10/1999 | Reedy et al. |
| 6,009,564 A * | 1/2000 | Tackles et al. .................. 2/436 |
| 6,038,707 A | 3/2000 | Ryden et al. |
| 6,119,276 A | 9/2000 | Newcomb et al. |
| 6,138,285 A | 10/2000 | Robrahn et al. |
| 6,513,171 B1 | 2/2003 | Soper |
| 6,550,914 B1 | 4/2003 | Kopfer |
| 6,601,240 B1 * | 8/2003 | Tsubooka ...................... 2/436 |
| 6,637,038 B1 | 10/2003 | Hussey |
| 6,665,885 B1 * | 12/2003 | Masumoto ..................... 2/436 |
| 2001/0029623 A1 | 10/2001 | Tsubooka |
| 2002/0104153 A1 | 8/2002 | Benedict et al. |

* cited by examiner

SPORT GOGGLE WITH IMPROVED VENTILATION

This application is a Continuation-in-Part of U.S. patent application Ser. No. 10/098,980 filed Mar. 15, 2002, now U.S. Pat. No. 6,637,038, which claims the benefit of U.S. Provisional Application No. 60/277,210, filed Mar. 19, 2001.

BACKGROUND OF THE INVENTION

1. Field of the Invention

The present invention relates to an improved goggle for sports and other activities where eye protection and improved vision are desirable. More particularly it relates to a goggle which incorporates a system of high and low pressure venting using focused air flow and goggle exhaust to facilitate the rapid circulation of air through the enclosed goggle thereby preventing fogging and other problems caused by conventional goggles with limited or no air flow through the eye cavity behind the lens. The device also features optional moisture absorbing, or air flow control filters dimensioned for cooperative attachment at an exhaust aperture to increase or decrease the venting of moisture from the device and to absorb moisture during use and storage.

2. Prior Art

Skiing, motorcycling, and other sports which incorporate goggles for eye protection have become an ever more popular recreational pastime in the United States and throughout the world. Goggles are also especially popular for the military in areas with blowing sand or during parachute jumps and similar operations.

Since goggles are generally worn over the eyes of a user, it is most important that the eyesight of the user not be impaired by the goggles being worn and if possible, be improved by the goggles covering the eyes. In cold climates and in freezing venues such as ski slopes and high altitudes an inherent problem encountering goggle wearing individuals is that of fogging.

Fogging is caused by the temperature differential created in the enclosed area formed behind the goggle lens and in front of the face of the wearer and the air exterior to the goggle. The face of the user radiates heat and tends to heat the air inside the goggle and behind the lens much like the windshield of a car tends to fog when the air inside the car is warmer than the air outside the car, thus causing fog or condensation on the window. Consequently, venting of the air inside the lens of a goggle is desirable to help overcome and prevent fogging of the lens that would inhibit the view of the wearer. Various patents have attempted to overcome the inherent tendency of goggles to fog in a cold environment.

U.S. Pat. No. 6,009,564, (Tackles) teaches a vented goggle; however, Tackles requires a plurality of tunnels or slots be formed in the mask portion of the goggle which are easily plugged by snow and especially ice if the skier falls or by dirt in a blowing sand environment. Tackles also lacks a low pressure system to pull air from the face cavity.

U.S. Pat. No. 5,652,965 (Crooks) teaches a non-fogging goggle, but Crooks also uses an elongated slot formed in the mask portion below the lens that is easily clogged and also lacks negative pressure venting.

U.S. Pat. No. 5,542,130 (Grabos) discloses a goggle with a ventilation adjustment assembly having a plurality of apertures in the lens with a shutter to close them to adjust the flow of air. Grabos lacks a focused air flow on the apertures and any negative pressure to pull air from the cavity.

U.S. Pat. No. 4,670,914 (Harris) teaches venting of a goggle like device. However, Harris lacks any positive pressure or negative pressure to aid in the flow.

U.S. Pat. No. 4,290,673 (Yamamoto) discloses ski goggles which have a heating means to heat the space between two lenses but lacks any pressurized ingress of air or low pressure evacuation of air from the internal cavity.

As such, there is a pressing need for a non-fogging goggle that will work in cold and harsh environments. Such a goggle should have air venting that is aided by focusing air moving toward the lens into the interior cavity at increased pressure. However, such a device should not be easily clogged or hard to clean. Additionally, such a goggle device should provide additional ventilation of the interior cavity by creating negative pressure at exit apertures from the interior cavity to help evacuate the air therefrom. Such a device would be further enhanced by the provision of filters to absorb moisture or regulate the amount of air moving through the device and allow for adjustment thereof.

SUMMARY OF THE INVENTION

Applicant's device is an improved goggle for use in skiing, motorcycling, and other sports and endeavors where the use of goggles is favored or required. The device features one or a plurality of intake apertures on the goggle lens or body which communicate with the eye chamber formed between the lens and the face of the wearer inside the goggle when mounted to a face. The intake apertures communicate air which in the herein disclosed device are positioned in a plurality of points on the goggle. At least one aperture communicates through the lens or the body of the goggle which holds the lens and receives air that is pressurized by a curved slot or channel formed on a lip extending in front of the lens. The channel is dimensioned to focus air currents from diverse angles created by wind or the moving wearer onto this lower lens aperture. A lower intake aperture underneath the lip also receives pressurized air from the air hitting the wearer's face and being forced into the lower intake aperture by the protruding lip. A third set of intake apertures is positioned under a lip that overhangs the top of the lens and causes air to redirect into the upper intake apertures under the upper lip.

A plurality of different venting apertures in both sides of the device thus communicate with the eye chamber and thereby vent air to the atmosphere. This venting is aided by a leading edge of the top of the goggle body and the two sides of the goggle body which is curved much like an airplane wing and creates lift or a low pressure area immediately adjacent to the side venting apertures to draw air out through the venting apertures from the eye chamber. Top venting apertures are also positioned just behind an upper lip that also creates negative pressure adjacent to the top venting apertures to aid in venting the eye chamber.

An optional insertable moisture trap filled with moisture absorbent material is dimensioned for cooperative engagement into one or both of the side venting apertures to aid in the adsorption of moisture from the eye chamber during storage or when the user is not in a moving condition and needs extra help in removal of moisture from the eye cavity. Also insertable would be a series of filters or apertures that can regulate the flow through the eye cavity by slowing or increasing the flow out of the side apertures.

It is an object of this invention to provide a goggle with one or a plurality of intentionally directed air flows which are targeted onto one or more intake apertures to pressurize the air entering them and the flow through the intake apertures and into and out of the eye chamber of the goggle.

Another objective of this invention is to provide such an improved goggle which uses shaped side and top edges adjacent to the lens to create low pressure zones adjacent to side and top vent apertures to draw air from the eye chamber.

An additional objective of this invention is to provide optionally insertable filter cartridges containing moisture adsorbent to aid in moisture evacuation from the eye chamber.

A still further object of this invention is the provision of air directional components that are not easily clogged by snow, ice, or dirt, and which can be easily cleaned.

Further objectives of this invention will be brought out in the following part of the specification, wherein detailed description is for the purpose of fully disclosing the invention without placing limitations thereon.

DETAILED DESCRIPTION OF PREFERRED EMBODIMENTS OF THE DISCLOSED DEVICE

Referring now to the drawings FIGS. 1–8 wherein similar parts of the invention are identified by like reference numerals, the figures disclose the improved sport goggle featuring active venting system to prevent fogging using both positive and negative air pressure to enhance air circulation therethrough. The goggle body 12 is shaped to conform to a human face on the inside surface 14. A lens 16 is operatively mounted in the body 12. In the current best mode, the lens is curved around the face to be positioned to wrap around in front of the user's eyes when worn on the face. An eye cavity 18 is formed when worn by the user and defined by the area between the user's face, the inside surface 20 of lens 16 and interior surface 22 of the goggle body 12.

The lens 16 in the current best mode of the device 10 would be a unitary lens featuring two lenses, separated by an insulating space therebetween to reduce fogging. The wrap around style of the lens allows the wearer to maintain most if not all of his peripheral vision, and tapering the lenses by making them thicker at the center and tapering that thickness to all edges reduces distortion. However, the device 10, due to the plurality of sources of pressurized incoming air and the formation of negative pressure adjacent to the side venting apertures 30, provides such increased air flow through the eye cavity 18 that it will work well with a single simple curved lens 16 of one piece construction, and such is anticipated.

One or a plurality of lower intake apertures 24 on each side of the lens 16 or on the body 12 communicate 16 between the outside atmosphere and the eye cavity 18. One or a plurality of upper intake apertures 26 on each side of the lens 16 communicate at the upper edge of the lens 16 between the atmosphere and the eye cavity 18.

Also provided in a current prefered mode of the device are one or a plurality of body intake apertures 25 which communicate through the body 12 into the eye cavity 18 below a protruding ledge 34 of the body 12 in front of the lower portion of the lens 16. While the device 10 will perform admirably without these body intake apertures 25, the preferred mode incorporates them and the flow through these apertures is enhanced by the increased pressure formed in front of the user's face and below the overhanging ledge 24 and this enhances the air flow through the eye cavity 18.

Venting of the eye cavity 18 is provided by a plurality of upper venting apertures 28 communicating through the body 12 at a top wall 19 providing air flow from the eye cavity 18 to the exterior atmosphere. Also providing venting of the eye cavity 18 are a plurality of side venting apertures 30 located on the sides of the body 12.

Improved venting through improved air flow into and out of the eye cavity 18 is achieved through the provision of both positive incoming pressure and negative air pressure adjacent to the side venting apertures. Positive incoming pressure is provided by the use of focusing channels 32 which are depicted as curved in shape and are situated on top of the ledge 34 formed on the front of the body 12 adjacent to the bottom portion of the lens 16. The focusing channels 32 are dimensioned and placed at an angle to the lower intake aperture 24 such that they act as a means to focus diverse air currents communicating with the front surface of the body 12 directly into the lower intake aperture 24. This focusing of diverse air currents thereby substantially increases the air volume and thus pressure communicated to the lower intake apertures 24 which is then communicated through the lens 16 or the body 12 and into the eye cavity 18 under pressure. The current preferred mode of the device 10 features a generally curved U-shaped groove forming the focusing channels 32 formed on top of the ledge 34 with the end of the channel which is deepest being adjacent the intake apertures 24. Having a channel 32 with an open top alleviates any clogging from dust, snow, or ice, which are simply blown off of the ledge during use. A channel air reflecting wall 35 rising highest adjacent to the lens 16 in the embodiment of FIG. 5 also helps reflect moving air onto the lens 16 and the adjacent lower intake aperture 24 when it communicates through the lens.

While the current preferred mode of the channel 32 is substantially U-shaped, other shapes are anticipated so long as the air traveling therethrough is channeled and focused upon the intake aperture 24 at the lens end of the focusing channels 32.

This provision of focusing channels 32 enhances the air flow from the front of the goggle 12 to the eye cavity 18 when the user is moving forward as is generally the case when skiing or riding a motorcycle or other motorized craft. The focusing channels 32 thus use this forward motion and the moving air to target diverse air currents substantially to a single point directly in front of the lower intake apertures 24, thereby forcing pressurized air into the lower intake apertures and thus into the eye cavity 18.

Additional air flow may be provided by an optional second focusing channel 33 which focuses and thus pressurizes moving air onto another lower intake aperture 24.

Additional air flow enhancement may also be provided by a second air pressurizing means adjacent to the upper intake apertures 26 through the provision of a pressurizing ridge 38 at a top edge of the lens 16 formed by the goggle body 12 which serves to impede the flow of air up the lens 16 on the exterior surface 40 of the lens 16. When the wearer is moving forward during use and moving air hits the lens 16, this pressurizing ridge 38 blocks the natural rising of air when it hits the exterior surface 40 of the lens 16 and creates a high pressure area adjacent to the upper intake apertures 26, thereby forcing air therethrough into the eye cavity 18 and aiding the flow therein.

To improve the air flow through the eye cavity 18 even more, a means to pull air from the eye cavity 18 is provided by the provision of a means to create negative air pressure adjacent to the side venting apertures 30 in the form of curved body surfaces 39 immediately in front of the two side venting apertures 30. Using this curved surface, which acts much like the leading and longer upper edge of an airplane wing, creates lift or a low pressure area 44 immediately adjacent to the side venting apertures 30 when the wearer is moving forward wearing the device 10, and moving air hits the curved body surfaces 39 and flows thereover. This low pressure area 44 helps venting of the eye cavity 18 by pulling air through the side venting apertures 30 due to the low pressure area 44 having lower air pressure than the higher pressure in the eye cavity 18. The combination of the pressure increases caused by one or all of the aforementioned lower intake apertures 24 and focusing channels 32 and 33 and the upper intake apertures 26 and pressurizing ridge 38, and the body intake apertures 25 under the ledge 34, along with the low pressure area 44 adjacent to the side venting apertures, serves to greatly increase the venting of air into and through the eye cavity 18 when the user is moving forward during use and creating moving air toward the device 10. Further air flow is also provided by the upper venting apertures 28 in the top wall 19 which are situated directly behind a curved top wall 19 which also acts much like an airplane wing when the user moves forward creating a second low pressure area 45, which aids in venting air through the upper venting apertures 28 from the eye cavity 18.

Additional enhancement to the performance of the device 10 is provided by an optional insertable aperture gate 48, which is dimensioned for cooperative frictional engagement inside the similarly shaped side venting apertures 30. The aperture gate 48 has a number of potential useful functions. In one use the aperture gate 48 may be filled with moisture absorbent material such as pearlite or other moisture absorbing substance to keep the goggles dry during storage and help pull moisture from a fogged goggle by temporary insertion during use, thereby using air flow and the absorbent to pull moisture from the eye cavity 18. In another configuration, the insertable aperture gate 48 could use a series of filters or apertures that would have differing air passage capability and can thus slow or increase the air flow through the side venting apertures 30 and provide a means to regulate the air flow through the eye cavity by slowing or increasing the flow out of the side venting apertures 30.

Figure 1:
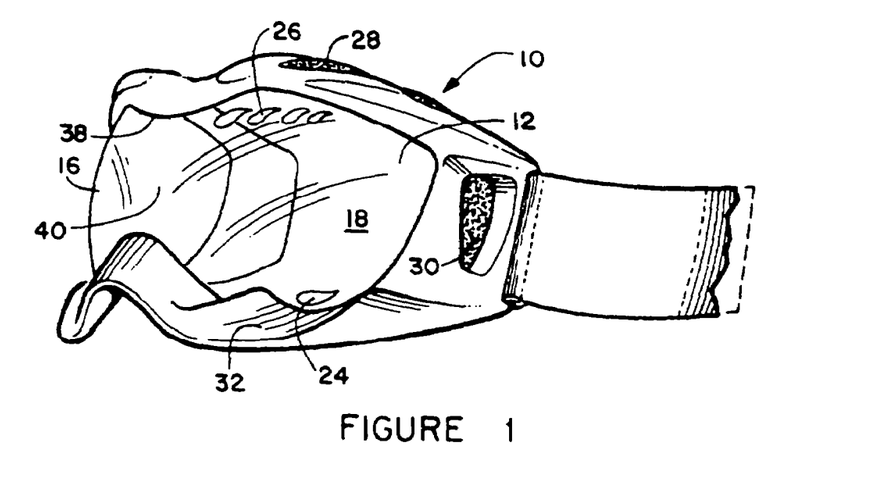
FIG. 1 is a perspective view of the disclosed device depicting the goggle body having air channels and protrusions formed to focus air currents directly onto intake apertures communicating through the lens.
Figure 2:
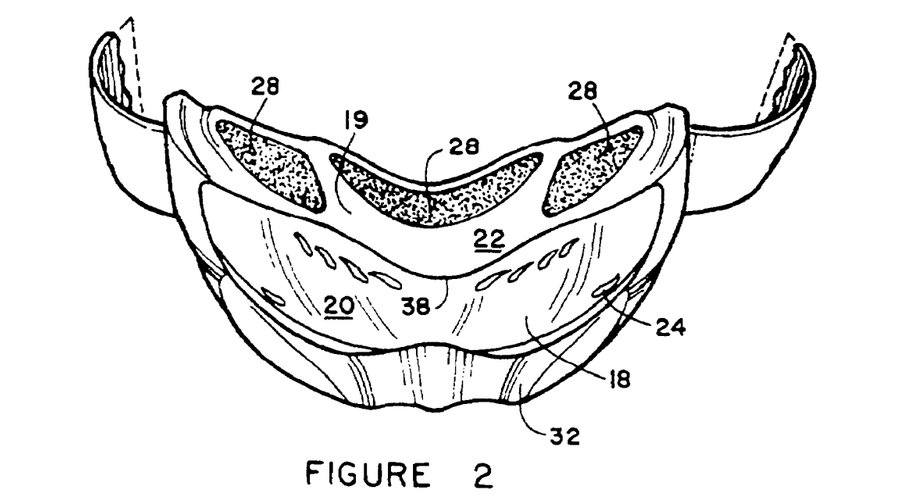
FIG. 2 is a top view showing the upper venting apertures located in the top of the goggle body and a top view of the shaped air channels on top of the protruding lower lip which target air to the intake apertures.
Figure 3:
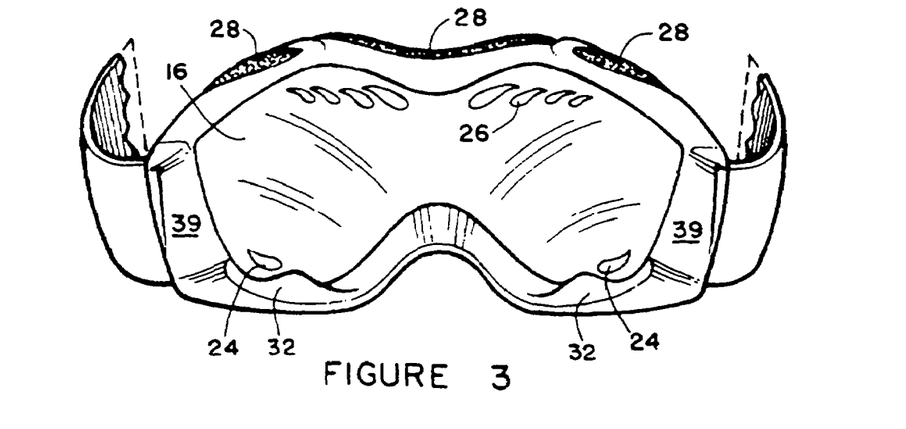
FIG. 3 is a front view of the disclosed goggle showing the formed air channel in the overhanging lip and a second optional channel for use with a second aperture in the lens.
Figure 4:
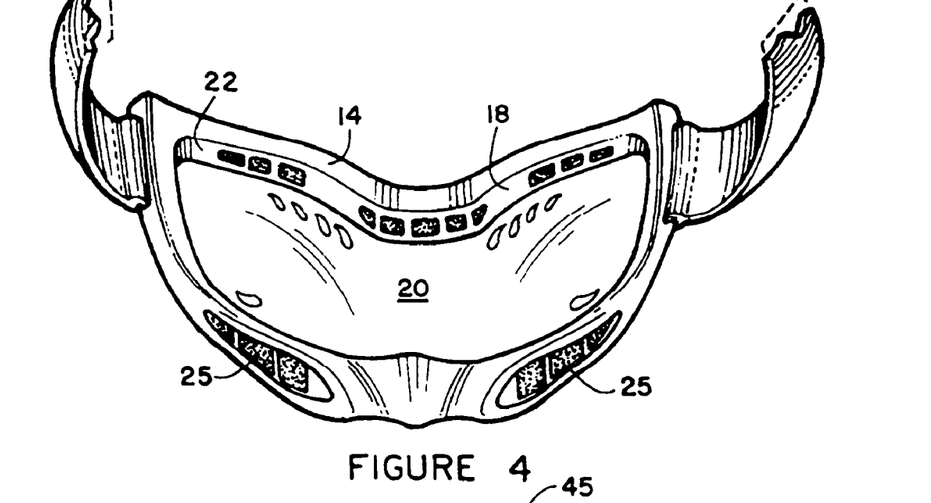
FIG. 4 is a rear view of the disclosed goggle showing the venting apertures and intake apertures communicating into the eye chamber.
Figure 5:
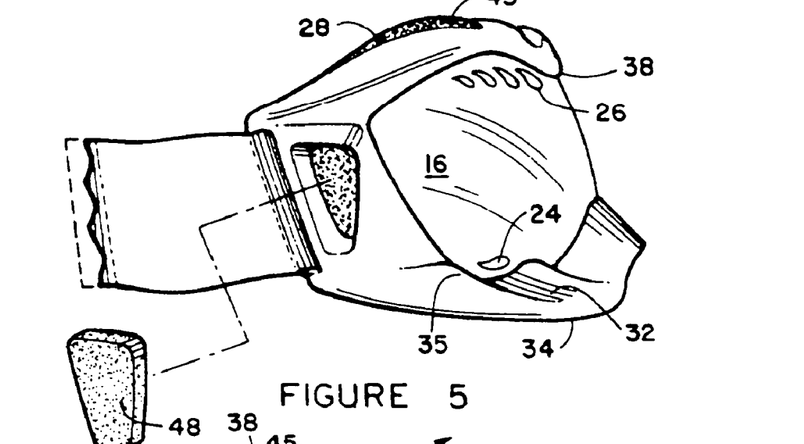
FIG. 5 depicts an embodiment of the device which features optional insertable filters or aperture adjusters dimensioned for cooperative engagement with the side venting apertures.
Figure 6:
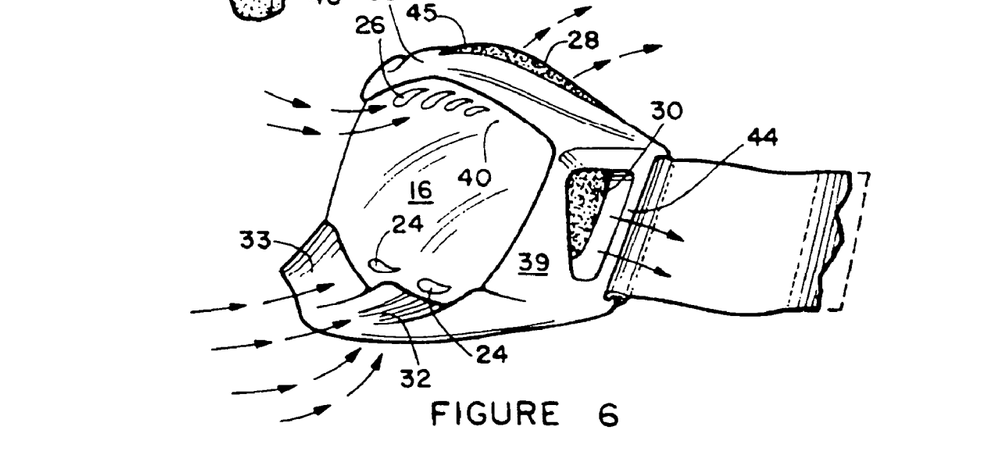
FIG. 6 depicts another side view of the goggle body showing the air currents focused over the curved edges in front of the side apertures, on the upper ridge, and lower ridge, and the channel formed in front of the lens apertures.
Figure 7:
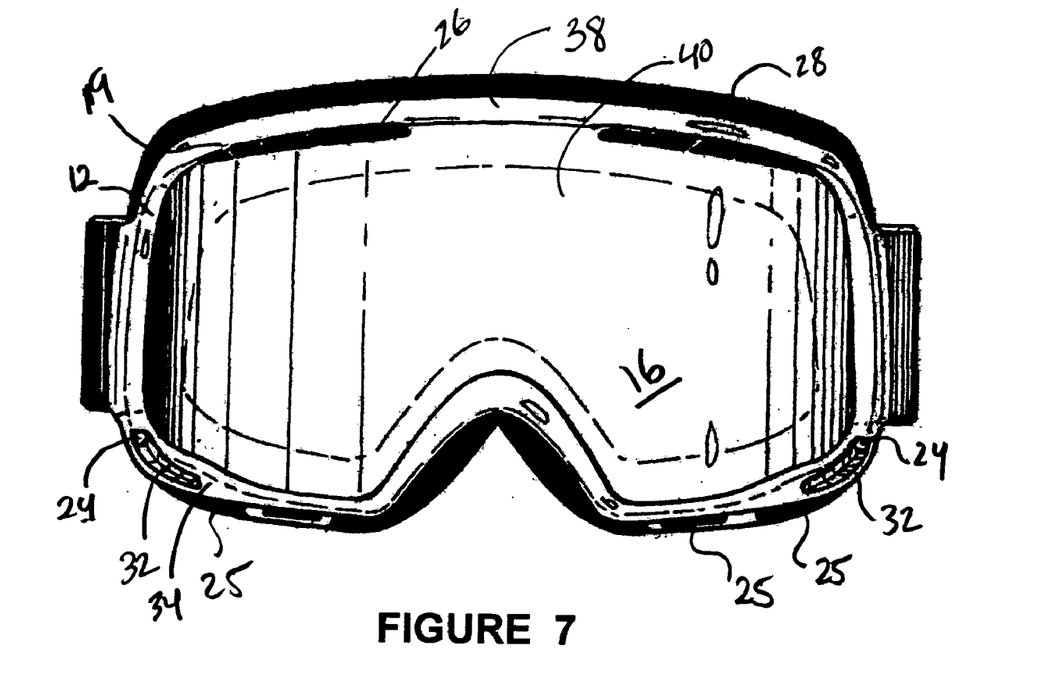
FIG. 7 depicts a front view of another preferred embodiment of the device herein disclosed wherein air is focused from diversed angles upon an intake aperture formed in the body of the goggle.
Figure 8:
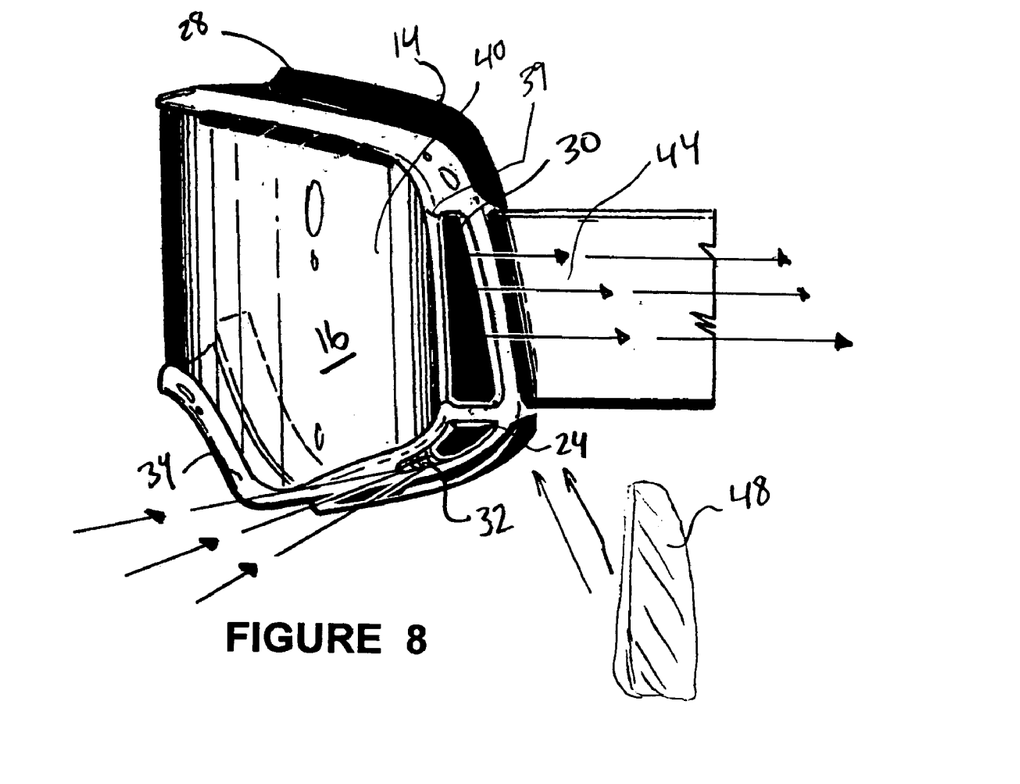
FIG. 8 shows a side view of the device of FIG. 7 and depicts the airflow being focused on the intake aperture by the channel and exiting from the venting aperture on the side.

An additional preferred embodiment of the disclosed device is shown in FIGS. 7 and 8. This embodiment functions substantially in the same fashion as that of FIGS. 1–6 but places one or a plurality of lower intake apertures 24 on the body 12 of the goggle which communicate between the outside atmosphere and the eye cavity 18. This embodiment would work especially well in cases where the goggle is being used in a manner that makes an aperture 24 in the lens 16 not as desirable such as during a paintball match where high speed paintballs might impact the lens 16 and the aperture 24 to create a weak point in the lens 16 that might allow it to crack. Also this embodiment would work well in cases where the aperture 24 in the lens 16 might tend to clog and not be easily cleaned during use in motocross dusty conditions or paintball where the paint from an impacting projectile might clog the lens aperture 24.

In the embodiment of FIGS. 7–8 incoming air from diverse angles is focused upon the lower intake aperture 24 formed in the body 12 through the provision of the same focusing channel 32 of the other preferred embodiment. Just as in the first embodiment, these focusing channels 32 are shown as curved in shape and are situated on top of the ledge 34 formed on the front of the body 12 and lens 16. The focusing channels 32 are dimensioned and placed at the appropriate approach angle to the lower intake aperture 24 formed in the body 12 such that they act as a means to focus diverse air currents communicating with the front surface of the body 12 and lens 16 directly into the lower intake aperture 24 formed in the body 12. This focusing of the diverse air currents substantially increases the air volume and thus pressure communicated to the lower intake apertures 24 in the body 12 which is then communicated from the intake aperture into the eye cavity 18 under pressure, much the same as the first embodiment.

This provision of focusing channels 32 formed in the ledge in front of the intake aperture 24 in the side edge of the body 12, enhances the air flow from the front of the goggle 12 to the eye cavity 18 when the user is moving forward as is generally the case when skiing, riding a motorcycle or other motorized craft, or running during a paintball match. The focusing channels 32 thus use this forward motion and the moving air from wind to target diverse approaching air currents substantially to a single point directly in front of or on the lower intake apertures 24 formed in the body 12 at a side edge, thereby forcing pressurized air into the intake apertures 24 which communicate it into the eye cavity 18.

The current preferred mode of this frame mounted intake aperture 24 embodiment of the device 10 features a generally curved U-shaped groove forming the focusing channels 32 which are formed on top of the ledge 34 with the end of the channel which is widest being adjacent the intake apertures 24. This embodiment having a channel 32 with an open top and forming the intake aperture 24 in the body 12 alleviates any clogging of the focusing channel 32 from dust, snow, ice, or paint which are simply blown off of the ledge during use. Further, placing the intake aperture 24 in the body 12 in communication with the eye cavity 18, alleviates making a hole in the lens 16 giving the lens 16 more strength during uses which have a high impact potential on the lens 16 such as paintball games and motocross at high speeds where bugs and rocks are a constant hazard.

Additional air flow may be provided just as in the first embodiment through one or a plurality of upper intake apertures 26 adjacent to the lens 16 which communicate at the upper edge of the lens 16 between the atmosphere and the eye cavity 18. Also provided in a prefered mode of this second preferred embodiment of the device 10 are one or a plurality of body intake apertures 25 which communicate through the body 12 with the eye cavity 18 from a position below a protruding ledge 34 of the body 12 in front of the lower portion of the lens 16. While the device 10 will perform admirably without these body intake apertures 25, the preferred mode of this second embodiment incorporates them and the flow through these body intake apertures 25 is enhanced by the increased pressure formed in front of the user's face and below the overhanging ledge 24, and this enhances the air flow through the eye cavity 18.

Venting of the eye cavity 18 is provided by a plurality of upper venting apertures 28 communicating through the body 12 at a top wall 19 providing air flow from the eye cavity 18 to the exterior atmosphere. Also providing venting of the eye cavity 18 are a plurality of side venting apertures 30 located on the sides of the body 12. Improved venting through improved air flow into and out of the eye cavity 18 is achieved in this second preferred embodiment through the provision of both positive incoming pressure from the focusing channels 32 on the intake apertures 24 as well as the negative air pressure adjacent to the side venting apertures 30 caused by the curved surface of the lens 16 and the frame 12 causing a wing like increase in air speed over the side venting apertures 30 and creating negative pressure adjacent to the venting apertures 30.

Should even more additional air flow be desired, it can be provided by an optional second focusing channel 33 which focuses incoming air currents on an intake aperture formed in the lens 16 as in FIGS. 1–6, concurrently with the focusing channel 32 which focuses incoming air currents on the intake aperture 24 formed at a side edge of the body 12, thus doubling the amount of pressurized air communicated to the eye cavity 18.

Much the same as the first prefered embodiment, additional air flow enhancement may also be provided by a second air pressurizing means adjacent to the upper intake apertures 26 through the provision of a pressurizing ridge 38 at a top edge of the lens 16 formed by the goggle body 12 which serves to impede the flow of air up the lens 16 on the exterior surface 40 of the lens 16. When the wearer is moving forward during use and moving air hits the lens 16, this pressurizing ridge 38 blocks the natural rising of air when it hits the exterior surface 40 of the lens 16 thus creating a high pressure area adjacent to the upper intake apertures 26 and thereby forcing air therethrough into the communicating eye cavity 18 aiding the flow therein.

Just as in the first preferred embodiment, air flow through the eye cavity 18 is improved even further through the provision of a means to pull air from the eye cavity 18 by creating negative air pressure adjacent to the side venting apertures 30. This means to create negative air pressure is provided in the form of curved body surfaces 39 and curved lens surface 40 immediately in front of the two side venting apertures 30. These curved surfaces act much like the leading and longer upper edge of an airplane wing which creates lift or a low pressure area 44 immediately adjacent to the side venting apertures 30 when the wearer is moving forward wearing the device 10 and moving air hits the curved body surfaces 39 and flows thereover. This low pressure area 44 helps venting of the eye cavity 18 by pulling air from the side venting apertures 30 due to the low pressure area 44 having lower air pressure than the higher pressure in the eye cavity 18. Much the same as the first embodiment, in this second preferred embodiment the combination of the pressure increase caused by one or both of the aforementioned lower intake apertures 24 and focusing channels 32 and 33, the upper intake apertures 26 and pressurizing ridge 38, and the body intake apertures 25 under the ledge 34, along with the low pressure area 44, adjacent to the side venting apertures serves to greatly increase the venting through the eye cavity 18 when the user is moving forward during use and creating moving air toward the device 10.

As best depicted in FIG. 8, additional enhancement to the performance of the device 10 is provided by an optional insertable aperture gate 48, which is dimensioned for cooperative frictional engagement inside the similarly shaped side venting apertures 30. The aperture gate 48 has a number of potential useful functions. In one use the aperture gate 48 may be filled with moisture absorbent material such as pearlite or other moisture absorbing substances to keep the goggles dry during storage and help pull moisture from a fogged goggle by temporary insertion during use, thereby using air flow and the absorbent to pull moisture from the eye cavity 18. In another configuration, the insertable aperture gate 48 could use a series of filters or apertures that would have differing air passage capability and can thus slow or increase the air flow through the side venting apertures 30 and thus provide a means to regulate the air flow through the eye cavity by slowing or increasing the flow out of the side venting apertures 30.

While all of the fundamental characteristics and features of the sport goggles with venting system for anti-fogging have been described herein, with reference to particular embodiments thereof, a latitude of modification, various changes and substitutions are intended in the foregoing disclosure, and it will be apparent that in some instances, some features of the invention will be employed without a corresponding use of other features without departing from the scope of the invention as set forth. It should be understood that such substitutions, modifications, and variations may be made by those skilled in the art without departing from the spirit or scope of the invention. Consequently, all such modifications and variations are included within the scope of the invention as defined herein.

What is claimed is:

1. A sport goggle for wearing on the face of a user having an improved air venting system to enhance air flow through the goggle, comprising:
   a goggle body having an exterior surface and an interior surface and having a lens aperture surrounded by a top wall, a bottom wall, and two sidewalls;
   a lens mounted in said lens aperture, said lens having a top lens portion adjacent to said top wall of said goggle body and a bottom lens portion adjacent to said bottom wall of said body;
   an eye cavity formed between the face of a wearer, the lens, and said interior surface of said goggle body when said goggle body is mounted on the face of said wearer;
   a ledge formed in said exterior surface of said goggle body projecting forward adjacent to said bottom lens portion;
   at least one lower intake aperture in said goggle body, said intake aperture in communication with said eye cavity;
   at least one venting aperture communicating through said goggle body with said eye cavity; and
   at least one channel formed in an upper surface of said ledge, said channel dimensioned to focus air approaching said channel from diverse angles, onto said lower intake aperture, whereby air volume entering said lower intake aperture is increased by said channel thereby pressurizing air flow through said lower intake aperture into said eye cavity wherein said air flow exits through said venting aperture.

2. The sport goggle as defined in claim 1 further comprising:
   said at least one venting aperture is located in a, side wall of said goggle body;
   said exterior surface of said goggle body between said lens and said venting aperture is a curved surface;
   a low air pressure area immediately adjacent to said venting aperture when moving air travels over said curved surface; and
   whereby air flow through said eye cavity is enhanced by said low pressure area acting to draw higher pressure air from said eye cavity through said venting aperture.

3. The sport goggle as defined in claim 2 further comprising:
   one or a plurality of upper intake apertures communicating with said eye cavity adjacent to said top wall.

4. The sport goggle as defined in claim 3 further comprising:
   a ridge projecting from said top wall adjacent to said upper intake apertures; and
   said ridge curved to direct airflow thereover creating an upper high air pressure area adjacent to said upper intake apertures whereby air flow communicating through said upper intake apertures with said eye cavity is pressurized.

5. The sport goggle as defined in claim 4 further comprising:
   one or a plurality of body intake apertures communicating through said bottom wall with said eye cavity.

6. The sport goggle as defined in claim 5 further comprising:
   one or a plurality of body venting apertures communicating through said top wall with said eye cavity;
   said ridge having a curved ridge surface shaped to direct air thereover to thereby create a second low air pressure area immediately adjacent to said body venting aperture when moving air travels over said curved ridge surface; and
   whereby air flow through said eye cavity is enhanced by said second low pressure area acting to draw higher pressure air from said eye cavity through said one or a plurality of body venting apertures.

7. The sport goggle as defined in claim 4 further comprising:
   one or a plurality of body venting apertures communicating through said top wall with said eye cavity.

8. The sport goggle as defined in claim 3 further comprising:
   one or a plurality of body intake apertures communicating through said bottom wall with said eye cavity.

9. The sport goggle as defined in claim 4 further comprising:
   one or a plurality of body venting apertures communicating through said top wall with said eye cavity.

10. The sport goggle as defined in claim 2 further comprising:
    one or a plurality of body intake apertures communicating through said bottom wall with said eye cavity.

11. The sport goggle as defined in claim 10 further comprising:
    one or a plurality of body venting apertures communicating through said top wall with said eye cavity.

12. The sport goggle as defined in claim 2 further comprising:
    one or a plurality of body venting apertures communicating through said top wall with said eye cavity.

13. The sport goggle as defined in claim 2 further comprising:
    an aperture gate dimensioned for cooperative engagement in said venting aperture, said aperture gate allowing air flow therethrough and having moisture absorbent material therein.

14. The sport goggle as defined in claim 1 further comprising:
    one or a plurality of upper intake apertures communicating with said eye cavity adjacent to said top wall.

15. The sport goggle as defined in claim 14 further comprising:
    a ridge projecting from said top wall adjacent to said upper intake apertures; and
    said ridge curved to direct airflow thereover creating an upper high air pressure area adjacent to said upper intake apertures whereby air flow communicating through said upper intake apertures with said eye cavity is pressurized.

16. The sport goggle as defined in claim 15 further comprising:
    one or a plurality of body intake apertures communicating through said bottom wall with said eye cavity.

17. The sport goggle as defined in claim 16 further comprising:
    one or a plurality of body venting apertures communicating through said top wall with said eye cavity;
    said ridge having a curved ridge surface shaped to direct air thereover to thereby create a second low air pressure area immediately adjacent to said body venting aperture when moving air travels over said curved ridge surface; and
    whereby air flow through said eye cavity is enhanced by said second low pressure area acting to draw higher pressure air from said eye cavity through said one or a plurality of body venting apertures.

18. The sport goggle as defined in claim 15 further comprising:
    one or a plurality of body venting apertures communicating through said top wall with said eye cavity.

19. The sport goggle as defined in claim 14 further comprising:
    one or a plurality of body intake apertures communicating through said bottom wall with said eye cavity.

20. The sport goggle as defined in claim 1 further comprising:
    one or a plurality of body intake apertures communicating through said bottom wall with said eye cavity.

21. The sport goggle as defined in claim 1 further comprising:
    one or a plurality of body venting apertures communicating through said top wall with said eye cavity.

22. The sport goggle as defined in claim 2 further comprising:
    an aperture gate dimensioned for cooperative engagement in said at least one venting aperture, said aperture gate allowing a determined amount of air flow therethrough to thereby provide a means to regulate the quantity of airflow through said venting aperture.

23. The sport goggle as defined in claim 1 further comprising:

at least one additional lower intake aperture in said lens, said intake aperture in communication with said eye cavity; and at least one additional channel formed in an upper surface of said ledge, said additional channel dimensioned to focus air approaching said channel from diverse angles, onto said additional lower intake aperture, whereby air entering said additional lower intake aperture is pressurized by said additional channel thereby pressurizing air flow through said additional lower intake aperture into said eye cavity wherein said air flow exits through said venting aperture.

24. The sport goggle as defined in claim 2 further comprising:

at least one additional lower intake aperture in said lens, said intake aperture in communication with said eye cavity; and at least one additional channel formed in an upper surface of said ledge, said additional channel dimensioned to focus air approaching said channel from diverse angles, onto said additional lower intake aperture, whereby air entering said additional lower intake aperture is pressurized by said additional channel thereby pressurizing air flow through said additional lower intake aperture into said eye cavity wherein said air flow exits through said venting aperture.

25. A sport goggle for wearing on the face of a user having an improved air venting system to enhance air flow through the goggle, comprising:

a goggle body having an exterior surface and an interior surface and having a lens aperture surrounded by a top wall, a bottom wall, and two sidewalls;

a lens mounted in said lens aperture, said lens having a top lens portion adjacent to said top wall of said goggle body and a bottom lens portion adjacent to said bottom wall of said body;

an eye cavity formed between the face of a wearer, the lens and said interior surface of said goggle body when said goggle body is mounted on the face of said wearer;

at least one lower intake aperture communicating through at least one of said lens or said goggle body, said intake aperture in communication with said eye cavity;

at least one venting aperture located in a sidewall of said goggle body, said venting aperture communicating through said goggle body with said eye cavity; and exterior surface dimensional means to direct airflow thereover to create negative air pressure immediately adjacent to said venting aperture, whereby air entering said eye cavity is pulled from said eye cavity by said negative air pressure adjacent to said venting aperture.

26. The sport goggle as defined in claim 25 wherein said exterior surface dimensional means to direct airflow thereover to create negative air pressure comprises:

said exterior surface of said goggle body between said lens and said venting aperture being a curved surface thereby increasing velocity of said airflow thereover and creating said negative air pressure adjacent to said venting aperture.

27. The sport goggle as defined in claim 26 further comprising:

one or a plurality of upper intake apertures communicating with said eye cavity adjacent to said top wall.

28. The sport goggle as defined in claim 26 further comprising:

one or a plurality of body intake apertures communicating through said bottom wall with said eye cavity.

29. The sport goggle as defined in claim 25 further comprising:

one or a plurality of upper intake apertures communicating with said eye cavity adjacent to said top wall.

30. The sport goggle as defined in claim 29 further comprising:

a ridge projecting from said top wall adjacent to said upper intake apertures; and said ridge curved to direct airflow thereover creating an upper high air pressure area adjacent to said upper intake apertures whereby air flow communicating through said upper intake apertures with said eye cavity is pressurized.

31. The sport goggle as defined in claim 30 further comprising:

one or a plurality of body venting apertures communicating through said top wall with said eye cavity; and said ridge having a curved ridge surface dimensioned to increase airflow speed thereover to thereby create a second low air pressure area immediately adjacent to said one or a plurality of body venting apertures when moving air travels over said curved ridge surface whereby air flow through said eye cavity is additionally enhanced by said second low pressure area acting to draw air from said eye cavity through said one or a plurality of body venting aperture.

32. The sport goggle as defined in claim 29 further comprising:

one or a plurality of body venting apertures communicating through said top wall with said eye cavity.

33. The sport goggle as defined in claim 25 further comprising:

one or a plurality of body venting apertures communicating through said top wall with said eye cavity.

34. The sport goggle as defined in claim 26 further comprising:

one or a plurality of body venting apertures communicating through said top wall with said eye cavity.

* * * * *

UNITED STATES PATENT AND TRADEMARK OFFICE
CERTIFICATE OF CORRECTION

| | | |
|---|---|---|
| PATENT NO. | : 7,137,153 B2 | Page 1 of 1 |
| APPLICATION NO. | : 10/695055 | |
| DATED | : November 21, 2006 | |
| INVENTOR(S) | : P.P. Hussey | |

It is certified that error appears in the above-identified patent and that said Letters Patent is hereby corrected as shown below:

<u>COLUMN</u>      <u>LINE</u>

9            7            "a, side" should read --a side--
(Claim 2,   line 3)

9            48           "claim 4" should read --claim 3--
(Claim 7,   line 1)

Signed and Sealed this

Twenty-second Day of May, 2007

JON W. DUDAS
*Director of the United States Patent and Trademark Office*